United States Patent [19]

Feeney et al.

[11] Patent Number: 5,801,269

[45] Date of Patent: Sep. 1, 1998

[54] PROCESSES FOR CYSTALLIZING 4, 4'-DIMETHYL BIBENZOATE (DMBB) RECOVERED FROM POLYESTER BYPRODUCT STREAMS

[75] Inventors: Carrie A. Feeney, Bridgewater, N.J.; Ida L. Jones, Charlotte, N.C.; Bennett C. Ward, Koenigstein, Germany; Thomas M. Kenesson; Charles B. Hilton, both of Corpus Christi, Tex.; Michael R. Ahern, Bayonne, N.J.; Gregory M. Adams, Corpus Christi, Tex.; Edward M. de la Garza, Corpus Christi, Tex.; B. Frank Wood, Jr., Corpus Christi, Tex.; Thomas L. Grantland, San Antonio, Tex.; Kan J. Tsai; James L. Ragan, both of Corpus Christi, Tex.

[73] Assignee: Hoechst Celanese Corp., Somerville, N.J.

[21] Appl. No.: 848,367

[22] Filed: Apr. 30, 1997

[51] Int. Cl.$^6$ ................................................. C07C 67/48
[52] U.S. Cl. ................................................................ 560/78
[58] Field of Search ................................................. 560/78

[56] References Cited

U.S. PATENT DOCUMENTS 3,277,153 10/1966 Pieroh .

*Primary Examiner*—Samuel Barts
*Attorney, Agent, or Firm*—John M. Genova

[57] ABSTRACT

Processes for recovering 4,4'-dimethyl bibenzoate (DMBB) from byproduct streams of dimethyl terephthalate (DMT) production are disclosed. The byproduct streams are treated to produce an overhead stream which includes DMBB. In one aspect of the invention, the overhead product stream is added to an organic solvent under conditions sufficient to rapidly form a suspension of crystallized DMBB. In another aspect of the invention, the overhead is dissolved in an appropriate organic solvent and cooled to form a suspension of DMBB crystals in the solvent. A portion of the suspension is removed, and the remaining portion of the suspension centrifuged to recover DMBB crystals. In still another aspect of the invention, the overhead stream is treated with an organic solvent to form a slurry of DMBB crystals, and the resultant slurry thermally treated to increase the concentration of DMBB crystals therein while also solubilizing any organic contaminants.

17 Claims, 2 Drawing Sheets

DMBB SOLUBILITY (x)
RECRYSTALLIZATION (□)

PROCESSES FOR CYSTALLIZING 4,4'-DIMETHYL BIBENZOATE (DMBB) RECOVERED FROM POLYESTER BYPRODUCT STREAMS

FIELD OF THE INVENTION

The present invention relates generally to processes for recovering byproducts of chemical synthesis, and more particularly to processes for recovering byproducts of polyester synthesis.

BACKGROUND OF THE INVENTION 4,4'-dimethyl bibenzoate (or DMBB) is a useful starting material for polyester synthesis. DMBB is particularly useful as a monomer or co-monomer for the production of high performance polyester fibers and films, including liquid crystal polymers (LCP's). DMBB can be used as a modifier in the production of polyesters to specifically influence the property profile of the resultant polymer, and to provide improved properties for articles produced therefrom, such as fibers, films, and molded parts.

Various synthetic routes can be used to produce DMBB. An overview of the formation of the preparation of DMBB is given, for example, in "Beilsteins Handbuchder der Organischen Chemie," Vol. 9 (I), page 927; Vol. 9 (II), page 665; and Vol. 9 (III), page 4519. According to this, DMBB can be prepared by a multi-stage synthesis in which 4,4'-dimethylbiphenyl ("ditolyl") is first oxidized with dichromate/sulfuric acid to get 4-methylbiphenyl-4'-carboxylic acid. This product is oxidized with alkaline permanganate solution to give 4,4'-biphenyldicarboxylic acid, and this latter compound is esterified with methanol.

DMBB can also be recovered from byproduct streams resulting from the synthesis of dimethyl terephthalate (DMT), a useful starting material for the production of polyethylene terephthalate (PET). Typically, DMT is produced commercially by the catalytic oxidation of xylene, followed by methanol esterification of the crude oxidation mixture. The crude dimethyl terephthalate thus prepared can be purified by distillation. Following distillation, there remains a dark, viscous residue which typically is disposed of by incineration or burning.

The residue resulting from DMT production is a complex mixture of various byproducts, including DMBB. DMBB recovered from DMT byproduct streams generally should have a purity of at least about 99.8% before it can be polymerized to form polyester useful for the production of fibers, films, molded products and the like.

There have been various proposals for recovering DMBB from DMT byproduct streams. For example, U.S. Pat. No. 3,277,153 discloses a process for isolating diphenyl polycarboxylic acid methyl esters from distillation residues of DMT production. In this process, terephthalic acid and dimethyl isophthalate are removed by distillation from the DMT distillation residue. The distillation residue is then digested in hot methanol or xylene. Insoluble material is removed, the clear solution thus obtained is freed of solvent, and the extracts obtained are worked up in a manner known in the art to give chemically uniform substances. This process, however, is extremely complicated, requiring multiple recrystallization from various solvents to isolate DMBB. Further, the products thus obtained generally contain unwanted residues of oxidation catalyst from the DMT production.

DE-A-2310824 discloses the isolation of DMBB from residues of DMT production by distillation and crystallization after a required heat treatment. The patent emphasizes that without the heat treatment, a large amount of undesired compounds are formed, making isolation of pure DMBB difficult. This process is limited, however, in that DMBB attained therefrom can be contaminated with amounts of other products, namely trifunctional compounds such as trimethyl 2,4'5-biphenyltricarboxylate. This contamination can be extremely deleterious to the preparation of polyesters using the DMBB monomer, because its presence even in trace amounts can lead to branching and cross-linking and thus making the resultant polymer unusable. This contamination has to be removed by repeated extraction of the product with a solvent, resulting in a compromise between loss of material and purity.

DE 4312491 discloses a process for isolating DMBB from the residues of the preparation of DMT and from secondary streams of DMT production. The patent states that residues of DMT production can be distilled to obtain a wax-like distillate which contains residual DMT. The distillate is treated under high pressure with an organic solvent, and the solution cooled and allowed to crystallize, resulting in a suspension of DMBB crystals.

The process described in DE 4312491 can be useful for recovering DMBB from DMT production byproduct streams on a laboratory or pilot scale. Commercializing this process, however, requires consistent reproduction of high purity DMBB in economically feasible yields, despite variations in the feedstream composition. It can be difficult to consistently reproduce the process disclosed in DE 4312491 on a laboratory or pilot scale to provide feasible yields of DMBB having a sufficient purity for downstream applications, and these difficulties can be magnified as the scale of production is increased to a commercial production scale. Further, variations in the composition of the DMT byproduct feed stream also can adversely impact the ability to consistently reproduce this process. Still further, this process can require high pressures to treat the distillate, thus increasing DMBB recovery costs. In addition, the purity and the yields of recovered DMBB could be improved relative to that reported in the patent.

In addition, crystallization times and recovery of the suspended DMBB crystals (for example by centrifugation) can be time consuming and difficult. Thus, DMBB crystallization and crystal recovery can be a time limiting factor for efficient processing and commercial production of DMBB.

Still further, DMBB recovery processes including those described above and others are typically batch processes. The batch processes can require increased cycle times because of the time required to crystallize DMBB to maximize DMBB purity and yields. Batch processing can be further complicated by difficulties in the recovery of DMBB crystals, which can be time consuming and difficult using conventional crystal recovery techniques, such as centrifugation.

SUMMARY OF THE INVENTION

The present invention provides processes for the recovery and purification of 4,4'-dimethyl bibenzoate (DMBB) from byproduct streams resulting from dimethyl terephthalate (DMT) production. The present invention can provide improved production times and efficiencies, and in particular, a reduction in the time required for crystallization and/or recovery of the DMBB. The improvement in crystallization and recovery times can be achieved with minimal or essentially no loss of product purity, and can result in improved product purity. Improved processing times can also be achieved with minimal loss of product. In addition, the processes of the invention can provide controlled, reproducible recovery and purification of DMBB in desirable yields from feedstreams having varying compositions (including varying concentrations of DMT), and can be suitable for commercial scale production of DMBB from DMT byproduct streams.

DMBB recovered and purified in accordance with the present invention is useful for the production of polyester polymers which in turn are useful for the production of fibers, films, molded products and the like. Still further, DMBB recovered in accordance with the present invention can be free of residual catalyst from DMT production. This can be important when producing polyester polymer which includes DMBB for applications which require minimal or no residual metal catalyst, e.g., the production of electrical components, such as capacitors.

In the invention, a residue or byproduct stream resulting from DMT production, which includes DMBB and residual DMT, is treated to concentrate DMBB. Generally, the DMT byproduct stream is distilled to separate DMBB from the DMT byproduct stream and to form a DMBB concentrate stream having a higher concentration of DMBB than the DMT byproduct stream. Distillation conditions can also be selected to separate organic compounds other than DMBB from the DMT byproduct stream which have a higher molecular weight than DMBB and to include these compounds as components of the DMBB concentrate stream. The presence of higher molecular weight compounds in the DMBB concentrate stream is believed to assist in selectively crystallizing DMBB.

For example, for DMT byproduct streams comprising about 15% or less by weight DMT, distillation conditions are preferably selected to form a low boiling point overhead DMBB concentrate stream comprising about 30% to about 60%, more preferably about 35% to about 50%, of the DMT byproduct stream. The remaining portion of the DMT byproduct stream remains as a high boiling point bottom stream. This split of the DMT byproduct stream can maximize DMBB concentration of the overhead stream. This split also can result in the presence of other organic byproducts of DMT production in the overhead stream which have a higher molecular weight than DMBB. This is particularly advantageous for DMT byproduct streams comprising less than about 10% DMT, in which case it has been found that overhead:bottom splits in the range of about 35:65 to about 50:50 can result in the presence of heavier compounds in the overhead, and improved DMBB recovery and purity.

In one embodiment of the invention (referred to herein as "rapid" or "crash" crystallization), after the DMT byproduct stream is distilled, the overhead is added an organic solvent, preferably a lower alkanol, and more preferably methanol, under conditions sufficient to form a suspension of DMBB crystals in the organic solvent substantially immediately upon addition of the overhead to the solvent. In effect, DMBB present in the overhead is immediately precipitated or "crashed" out of the organic solution upon addition of the overhead to the solvent. This is in contrast to a process wherein the recovered overhead is solubilized in the organic solvent to form a solution thereof, and the solution is thereafter cooled to allow DMBB to crystallize over a period of time.

Preferably, the overhead is added to a solvent at a predetermined filtration temperature. As used herein, the term "filtration temperature" refers to a temperature of the organic solvent which is below that temperature at which DMBB begins to precipitate in the solvent with minimum or no precipitation of the additional components which can be present in the solution. In a preferred embodiment of the invention, the organic solvent is methanol heated to about 40° C. to about 50° C.

Although precipitation occurs rapidly and with minimal control of crystallization conditions, the inventors have found that in this embodiment of the invention DMBB crystals recovered after rapid crystallization can have relatively high purities of at least about 90%, preferably at least about 95%, and up to about 97% and higher. Further, increased purities can be obtained with minimal loss of percent recovery at this crystallization stage, i.e., at least about 40% recovery. Because precipitation occurs substantially immediately, lengthy solution cooling times can be avoided, thus improving the efficiencies of DMBB recovery.

After cooling, the crystals are recovered, for example, by centrifugation, washed and dried. The recovered crystals can be further purified to a purity of at least about 99.8%, and higher, by recrystallization as described below. DMBB can be recovered after recrystallization in yields approaching about 90%, and higher.

Overall yields of this embodiment of the invention (distillation, rapid crystallization and recrystallization) can be at least about 25%, preferably at least about 30%, and more preferably at least about 40%.

In another embodiment of the invention (referred to herein as "solvent reduction" recovery of DMBB crystals), after the DMT byproduct stream is distilled, the overhead is added to an organic solvent, preferably a lower alkanol, and more preferably methanol, to form a solution. Preferably, the overhead stream has a sufficient concentration of high molecular weight organic compounds so that pressure required to solubilize the overhead is minimized, i.e., the overhead can be solubilized at about atmospheric pressure, or slightly above atmospheric pressure.

The solution is thereafter cooled under controlled cooling rate conditions to selectively crystallize DMBB from the solution. Preferably, the solution is cooled under controlled cooling rate conditions from an initial solubilizing temperature (i.e., the temperature at which the overhead product goes into solution) to a predetermined filtration temperature. The predetermined filtration temperature is selected to precipitate DMBB with minimum or no precipitation of the additional components which can be present in the solution. Advantageously, when using methanol as a solvent, cooling ceases at a filtration temperature of about 40° C. to about 50° C. Preferred cooling rates are about 0.1° C. to about 1.0° C. per minute, and more preferably about 0.15° C. to about 0.5° C. per minute.

After cooling, the crystals are recovered by centrifugation, washed and dried, preferably removing about 65% to 100% of the solvent. As noted above, recovery of DMBB crystals, for example by centrifuging the suspension or slurry which includes crystallized DMBB, can be a time limiting factor in the recovery of DMBB from DMT byproduct streams. Centrifuging the slurry is time consuming, typically ranging from about 30 to about 120 minutes, and can be difficult because of the nature of the slurry and the DMBB crystals, i.e., the crystals are not readily separated from the slurry. In this embodiment of the present invention, processing times, and in particular centrifugation times, can be improved by reducing the total volume of liquid present in the slurry or suspension by removing a portion of the organic solvent prior to recovering DMBB crystals by centrifugation. Further efficiencies can be obtained by crystallizing additional batches of the DMT byproduct stream and reducing the liquid volume thereof prior to centrifugation, i.e., multiple batches of DMT byproduct streams can be processed in various stages due to the reduced centrifugation times that result.

In the initial crystallization step of this embodiment of the invention, the recovered DMBB crystals can have relatively high purities of at least about 90%, preferably at least about 95%, and up to about 97% and higher. Further, increased purities can be obtained with minimal loss of percent recovery. That is, in this initial crystallization step, DMBB recovery can be at least about 45%, preferably at least about 55%, and more preferably at least about 65%.

The recovered DMBB crystals can be further purified by recrystallization (described below) to a purity of at least about 99.8%, and higher, to provide a total recovery of DMBB (after distillation, crystallization, solvent removal and recrystallization) of greater than about 25%, preferably at least about 40%, more preferably at least about 50%, for the overall process in this embodiment of the invention.

In yet another embodiment of the invention, (referred to herein as "continuous" crystallization) after the DMT byproduct stream is distilled, the overhead is added to an organic solvent, preferably a lower alkanol, and more preferably methanol, under conditions sufficient to precipitate DMBB and to form a suspension of DMBB crystals in the organic solvent. Preferably, the temperature of the organic solvent is at or below the temperature at which DMBB begins to precipitate in that solvent system so as to substantially immediately precipitate DMBB (for methanol, less than about 55° C.). In effect, DMBB is rapidly precipitated or "crashed" out of the overhead. Again, this is in contrast to solubilizing the overhead in the organic solvent to form a solution, and thereafter cooling the solution to allow DMBB to crystallize over a period of time. Rapidly crystallizing DMBB in this manner can afford time savings, and can maximize DMBB crystal concentration. Preferably, in this embodiment of the invention, the organic solvent is methanol, and the temperature of the methanol is selected to provide a DMBB precipitation temperature of about 20° C. to about 30° C.

The resultant slurry is then thermally treated to increase the concentration and purity of the DMBB crystals. In this regard, typically organic compounds other than DMBB are also present in the overhead product and can also precipitate during DMBB precipitation. This is particularly true when the DMBB is rapidly crashed out of the overhead at low temperatures. Preferably, the slurry is thermally treated at a second temperature which is greater than the DMBB precipitation temperature to solubilize organic crystals other than DMBB, without solubilizing the DMBB crystals. Thus, although impurities may be initially present in the slurry, thermal treatment can effectively reduce or minimize the impurities.

The slurry can be thermally treated by washing the slurry with additional heated solvent in a vessel which is separate from the precipitation or crystallization vessel. A preferred wash solvent is methanol heated to about 30° C. to about 45° C.

The thermally treated slurry of DMBB crystals can be subjected to additional thermal treatment steps, each of which is conducted at a higher temperature than the last, for example, about 45° C. to about 55° C. The thermal treatment temperatures should not, however, exceed the temperature at which DMBB is solubilized in the organic solvent, so as to minimize loss of DMBB product.

In this embodiment of the invention, although precipitation occurs rapidly and with minimal control of crystallization conditions, it is currently believed that the DMBB crystals can have relatively high purities of at least about 90%, preferably at least about 95%, and up to about 97% and higher. Further, it is currently believed that increased purities can be obtained with minimal loss of percent recovery at this stage, i.e., at least about 45%, preferably at least about 50% recovery. In addition, because precipitation occurs substantially immediately, lengthy solubilizing and solution cooling times can be avoided, thus improving the efficiencies of DMBB recovery.

The crystals can be recrystallized to a purity of greater than 99.8%, and higher. The DMBB crystals can be directly recrystallized from the thermal treatment step without the need for intermediate and often time consuming crystal recovery steps (for example, centrifugation). Thus, this embodiment of the invention utilizing "continuous DMBB crystallization" can provide improved processing times and efficiencies in this regard as well.

BRIEF DESCRIPTION OF THE DRAWINGS

Some of the features and advantages of the invention having been described, others will become apparent from the detailed description which follows, and from the accompanying drawings, in which.

DETAILED DESCRIPTION OF PREFERRED EMBODIMENTS

Different process and apparatus embodiments of the invention are described below. While the invention is described with reference to specific processes and apparatus, it will be understood that the invention is not intended to be so limited. To the contrary, the invention includes numerous alternatives, modifications and equivalents as will become apparent from a consideration of the forthcoming discussion and the following detailed description.

Figure 1:
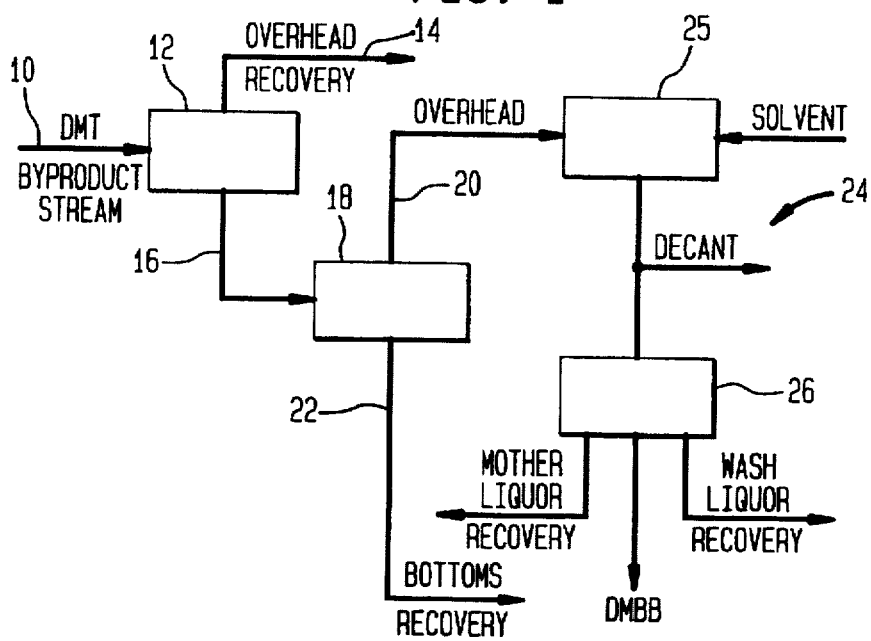
FIG. 1 is a flow chart illustrating processes for recovering and crystallizing 4,4'dimethyl bibenzoate (DMBB) from byproduct streams of DMT production using rapid crystallization and solvent reduction techniques.

FIG. 1 is a flow diagram illustrating a process in accordance with the invention for recovering 4,4'-dimethyl bibenzoate (DMBB) from byproduct streams resulting from dimethyl terephthalate (DMT) production. As discussed above, DMT is typically commercially produced by catalytic oxidation of xylene, reaction of the crude oxidation mixture with methanol, and subsequent distillation of the crude DMT. In this distillation, a dark viscous residue results, comprising a complex mixture of various byproducts of DMT production, including DMBB.

In the present invention, a byproduct stream from DMT production, indicated generally as 10 in FIG. 1, is treated to recover and purify DMBB present therein. Byproduct stream 10 is a residue or byproduct stream of DMT production comprising about 15% or less DMT, resulting from a series of distillations of the DMT product.

Preferably, byproduct stream 10 comprises DMT in an amount of about 0.5% to about 15% by weight, more preferably about 0.5% to about 10% by weight. This can be achieved, for example, by initially thermally or chemically treating a DMT production byproduct stream from which DMBB is to be recovered to reduce the DMT content thereof. For example, a DMT production byproduct stream which includes 25% by weight DMT, or less, can be heat treated to provide a byproduct stream having from about 5% to about 15% DMT. Alternatively, methanolysis can be used to chemically treat such a byproduct stream to reduce DMT content to about 1%, or less, preferably about 0.5%.

Referring again to FIG. 1, byproduct stream 10 is directed to a DMT separation unit 12, such as a suitable flasher, within which stream 10 can be subjected to an initial DMT separation step. Although not required, separation unit 12 can be advantageous to separate at least a portion of DMT present in the feed stream when the byproduct stream 10 has an initial DMT concentration greater than about 8%.

When present, unit 12 is operated at a temperature and pressure sufficient to remove at least about 2% to about 20%, and higher, of the DMT present in byproduct stream 10, with minimal or no decomposition of the heavier materials in the byproduct stream. Preferably, separation unit 12 is operated at a temperature from about 230° C. to about 250° C. and a pressure from about 20 to about 40 mm mercury (Hg), and more preferably a temperature of about 240° C. and a pressure of about 30 mm Hg. Unit 12 can be selected from apparatus conventional in the art for separating compounds based upon different physical properties thereof, e.g., different boiling points.

As illustrated in FIG. 1, the initial separation step results in the production of at least two product streams, a low boiling point overhead stream comprising DMT, indicated as 14, and a high boiling point bottom stream, comprising DMBB and DMT, indicated as 16. Overhead stream 14 can be directed to conventional recovery units as known in the art for downstream processing or disposal of organic compounds such as DMT.

Product stream 16 typically comprises DMT in amounts ranging from about 0.5% to about 15% by weight, and DMBB in amounts ranging from about 1% to about 5% by weight. The amount of DMT and DMBB in product stream 16 can vary at least in part based upon the composition of the DMT byproduct feed stream 10.

Product stream 16 is next directed to a DMBB separation unit 18 to separate DMBB from stream 16 and to concentrate DMBB. Advantageously, DMBB separation unit 18 is an evaporator, and preferably a thin or wiped film evaporator as known in the art. Generally, stream 16 is distilled within unit 18 under conditions selected to control the composition of the overhead stream, i.e., to maximize DMBB content of the overhead, as well as to include other organic compounds which are heavier than DMBB in the overhead stream.

For example, for a stream 16 which comprises about 15% or less by weight DMT and about 1% to about 5% DMBB, preferably distillation conditions are selected so that about 30% to about 60%, preferably about 35% to about 50%, of stream 16 forms a low boiling point overhead DMBB concentrate stream 20 in which the concentration of DMBB is higher than the concentration of DMBB in stream 16. The remaining portion of stream 16 remains as a high boiling point bottom stream 22. Stated differently, preferably distillation conditions are controlled to provide from about a 30/70 to about a 60/40 overhead/bottoms split of feed stream 16. The conditions of pressure and temperature of evaporator 18, however, should not exceed that at which high molecular weight constituents of stream 16 decompose or break down into their constituent components.

The overhead:bottom split can vary, depending upon feedstream composition, particularly DMT composition (which is generally the lightest component of the feedstream), so long as the overhead includes heavier molecular weight compounds. For example, the inventors have found that for feedstreams comprising less than about 10% DMT, overhead:bottom splits ranging from about 35:65 to about 50:50 can result in higher molecular weight compounds being included in the overhead split, and surprisingly in improved DMBB recoveries and/or purities downstream. For feedstreams having greater than about 10% DMT, the overhead split can be smaller (about 30%). However, with these higher initial DMT levels, it is surprising that DMBB can be effectively recovered at all, and such recoveries are believed to be aided by the presence of the heavier compounds in the overhead split.

The pressure of evaporator 18 can range from about 5 to about 20 mm Hg, and preferably is about 12 mm Hg. The temperature of evaporator 18 can also vary, ranging from about 270° C. to about 300° C., and preferably is about 280° C. Under these conditions, overhead stream 20 includes about 1% to about 10%, and higher, DMBB, and about 1.5% to about 15% by weight DMT, with other organic compounds (including higher molecular weight compounds) which result from DMT synthesis making up any remaining percentage. Organic compounds having a higher molecular weight than DMBB generally include biphenyls and benzylesters, which can be present in the overhead stream in amounts ranging from about 5% to about 40%, depending upon the composition of the DMT byproduct stream. Units 12 and 18 can also be combined, for example, as a fractional distillation column.

Controlling distillation conditions to concentrate DMBB and to include heavier molecular weight compounds in the low boiling point overhead stream can be advantageous for improved processing of the overhead, and for improved percent recoveries and purity in subsequent DMBB crystallization. Although not wishing to be bound by any explanation of the invention, it is believed that the presence of the higher molecular weight compounds in the overhead can assist selective crystallization of DMBB (i.e., crystallize DMBB while maintaining other organic compounds such as DMT and isomers of DMBB in solution). It is also believed that the presence of higher molecular weight compounds in the overhead assists in reducing and minimizing pressure conditions required to solubilize the overhead, i.e., the overhead can be solubilized under generally atmospheric conditions, thus reducing energy and equipment costs.

Bottoms product stream 22 can be directed to conventional recovery zones and thereafter disposed of, for example, by incineration or burned for fuel value.

Overhead product stream 20 is thereafter directed to a conventional condenser (not illustrated), and the condensate is directed to a DMBB recovery zone 24, which includes a crystallizer 25. The temperature of condensate directed from the condenser to crystallizer 25 advantageously ranges from about 70° C. to 100° C.

In one embodiment of the invention, DMBB is rapidly crystallized from the condensate ("rapid" or "crash" crystallization). Specifically, condensate from overhead product stream 20 is added to an organic solvent under conditions sufficient to form a suspension of DMBB crystals in the organic solvent substantially immediately upon addition of the overhead to the solvent. In effect, DMBB present in the overhead is substantially immediately precipitated or "crashed" out of solution upon addition of the overhead to the solvent. Such "immediate precipitation" can begin as quickly as 0 to 30 minutes after overhead is added to the solvent, and typically DMBB crystallization is completed within 0 to 15 minutes after addition of overhead.

Preferably, the overhead is added to solvent heated to a predetermined DMBB filtration temperature. The DMBB filtration temperature of the solvent is a temperature at or below which DMBB begins to precipitate in the solvent. The temperature of the solvent, however, should not be so low that other compounds which may be present in the overhead also begin to precipitate. As the skilled artisan will appreciate, the filtration temperature of the solvent can vary depending upon factors such as the type solvent used, the concentration of the various organic compounds in the overhead stream, the temperature of the overhead, and the like. Preferably, the organic solvent is methanol heated to about 40° C. to about 50° C. prior to addition of the overhead product.

The amount of organic solvent can vary, ranging from about 0.5 to about 2.0 times the weight of the condensate, and preferably is about 1 times the weight of the condensate (i.e., organic solvent and overhead condensate are mixed in substantially equal weight quantities). Higher and/or lower quantities of organic solvent can be used, but as the skilled artisan will appreciate, too much or too little can result in loss of material, decreased purity of the recovered product, and the like.

Substantially immediately after addition of the organic solvent to the overhead product, recovery of the DMBB crystals can begin, for example, as illustrated in FIG. 1 using a conventional centrifuge 26. Centrifugation is conducted for a time period sufficient to separate DMBB crystals from the slurry. The time for centrifugation can vary, ranging from about 30 to about 120 minutes, although greater or lessor time periods can be used.

Conditions for centrifugation, such as centrifugation temperatures, speeds, and load rates, can vary, depending upon the percentages of the various constituents of the feed stream 20. For example, for streams having higher DMT concentrations (i.e., greater than about 5%), and/or higher concentrations of organic compounds heavier than DMBB, preferably the slurry is added to centrifuge 26 using relatively low load rates (about 3 kilograms per minute), and centrifugation is conducted at lower temperatures, ranging from about 40° C. to about 50° C. In contrast, for streams having lower DMT concentrations (i.e., greater than about 5%), and/or higher concentrations of organic compounds heavier than DMBB, the slurry can be added to the centrifuge substantially at one time, and the centrifuge can be operated at higher temperatures, ranging from about 50° C. to about 60° C.

After the crystals of DMBB are separated from the slurry by centrifugation, the crystals are advantageously washed one or more times with the same or a different organic solvent, to remove any adsorbed impurities. Preferably, the organic wash is added substantially immediately upon slurry addition to the centrifuge to prevent or minimize crystallization of undesired contaminants, such as 4,4'-dicarbomethoxy benzophenone (DCMB).

Wash conditions, such as the amount of and temperature of the wash liquor, are selected to minimize loss of the desired DMBB product and impurities of the product. For example, for methanol, the temperature of the wash preferably is less than about 50° C. and the ratio of methanol to DMBB crystals can range from about 10:1 to about 20:1.

Thereafter, the wash liquor and mother liquor can be recovered and recycled or disposed of, and crude DMBB crystals are recovered and dried.

Suitable organic solvents for carrying out the process of the invention include lower alkanols having from 1 to 8, preferably 1 to 4, carbon atoms, in particular methanol. Other organic solvents can be used, including petroleum fractions having a boiling point of about 50° C. to 150° C., such as petroleum ether or ligroin, chlorinated hydrocarbons such as methylene chloride, chloroform, trichloroethylene, perchloroethane or monochlorobenzene, linear or cyclic ethers such as diethyl ether, tetrahydrofuran or dioxane, lower ketones such as acetone or methyl ethyl ketone or monocyclic aliphatic or aromatic solvents such as cyclohexane, benzene, toluene or xylenes. Other exemplary organic solvents include acetic acid and acetophenone. Preferred organic solvents include the lower alkanols described above, and in particular methanol and ethanol.

In this embodiment of the invention, because the organic solvent is added to the overhead product at the desired filtration temperature, the resultant slurry does not have to be cooled to crystallize DMBB. This can result in substantial time savings in the DMBB recovery process. Although precipitation occurs rapidly and with minimal control of crystallization conditions, the inventors have found that the recovered DMBB crystals can have relatively high purities of at least about 90%, preferably at least about 95%, and up to about 97% and higher, as determined using gas chromatographic analysis. Increased purities can be obtained with minimal loss of percent recovery at this stage, i.e., at least about 40%, preferably at least about 45%, more preferably at least about 50%, recovery.

In another embodiment of the invention, the condensate of overhead product stream 20 is added to an organic solvent in crystallizer 25 to form a solution of the condensate in the organic solvent. As discussed above, the presence of higher molecular weight compounds in the condensate is believed to assist in solubilizing the condensate under generally atmospheric pressure conditions (i.e., at or slightly above atmospheric pressure). The temperature of the organic solvent is sufficiently high to dissolve overhead product stream 20, and preferably is at least about the boiling point of the organic solvent or higher. For example, when using methanol, a preferred organic solvent, advantageously methanol temperature in the crystallizer 25 is at least about 65° C. (the boiling point of methanol at atmospheric pressure) and can range from about 65° C. to about 80° C. Higher temperatures and/or pressures can be necessary as the percentage of compounds heavier than DMBB is decreased, and/or the percentage of lighter compounds increased, in stream 20, in order to form a solution of the DMBB.

The amount of organic solvent can vary in this aspect of the invention, ranging from about 0.5 to about 2 times the weight of the condensate, and preferably about 1 times the weight of the condensate (i.e., organic solvent and overhead condensate are mixed in substantially equal weight quantities). Higher and/or lower quantities of organic solvent can be used, but as the skilled artisan will appreciate, too much or too little solvent can result in loss of material, decreased purity of the recovered product, and the like.

Residence time can vary, again depending upon the concentration of DMT. For example, for streams having higher DMT concentrations (i.e., greater than about 5% by weight), preferably residence time is minimized and the solution is substantially immediately cooled after formation. In contrast, for streams having lower DMT concentrations (less than about 5%), residence times can be longer, ranging from about 45 to about 90 minutes, and more preferably about 60 minutes, to insure substantially complete dissolution of DMBB in the organic solvent.

The solution is then cooled under controlled cooling rate conditions to selectively crystallize DMBB from the solution. Controlled cooling rate conditions can be advantageous to selectively crystallize DMBB while maintaining undesired contaminants in solution. As discussed above, it is believed that the presence of higher molecular weight compounds can assist in selectively crystallizing DMBB, i.e., can maintain the solubility of other organic compounds, such as DMT and isomers of DMBB which generally have lower molecular weights than DMBB.

Preferably, the solution is cooled by controlling the rate of cooling from an initial solubilizing temperature (i.e., the temperature at which stream 20 is solubilized) to a cooler predetermined filtration temperature. The solution is cooled at a rate of about 0.1° C. to about 1.0° C. per minute, and preferably at a rate of about 0.15° C. to about 0.5° C. per minute. The filtration temperature should be selected to selectively precipitate DMBB in solution, with minimal or no precipitation of additional components in the solution. Advantageously, when using methanol as a solvent, cooling ceases at a filtration temperature of about 40° C. to about 50° C.

The time to complete precipitation and crystallization can vary, and generally ranges from about 60 minutes to about 180 minutes, preferably about 90 minutes. This results in a suspension of DMBB crystals which are subsequently recovered.

The DMBB crystals can be recovered as illustrated in FIG. 1 using a centrifuge 26. Centrifugation is conducted for a time period sufficient to separate DMBB crystals from the slurry. As noted above, centrifuging the suspension or slurry which includes crystallized DMBB can be a time limiting factor in the recovery of DMBB from DMT byproduct streams. Centrifuging the slurry is time consuming, typically ranging from about 30 to about 120 minutes, and can be difficult because of the nature of the slurry and the DMBB crystals, i.e., the crystals are not readily separated from the slurry.

Processing times, and in particular centrifugation times, can be greatly improved in accordance with this embodiment of the present invention by reducing the total volume of liquid present in the slurry prior to centrifugation. To minimize loss of crystallized DMBB, the solid components of the slurry (i.e. DMBB crystals) are allowed to settle, typically over a period of about 30 to 45 minutes. The total volume of the liquid portion of the slurry can then be effectively reduced by removing a portion of the liquid thereof (which includes the organic solvent, as well as other organic compounds dissolved therein) with minimal loss of DMBB crystals. Preferably the liquid volume of the slurry is reduced about 20 to about 40 percent, and more preferably about 25 to about 35 percent, for example by pressure decantation, prior to centrifuging the suspension.

The time required to recover the DMBB crystals is at least about 2 times faster, and more preferably at least about 3 times faster, as compared to centrifugation times without removal of a portion of the suspension. The time for centrifugation in accordance with the invention can vary, and generally ranges from about 10 to about 30 minutes.

Conditions for centrifugation, such as centrifugation temperatures, speeds, and load rates, can be as described above with regard to "crash" crystallization.

Further efficiencies can be obtained in accordance with the process of the invention by crystallizing additional batches of the DMT byproduct stream and reducing the liquid volume thereof prior to centrifugation, i.e., multiple batches of DMT byproduct streams can be processed in various stages due to the increased centrifugation times that result.

After the crystals of DMBB are separated from the slurry by centrifugation, the crystals can be washed one or more times with the same or a different organic solvent, to remove any adsorbed impurities, also as described above.

Suitable organic solvents for carrying out this embodiment of the process of the invention include the solvents noted above.

The recovered DMBB crystals from this initial crystallization in this embodiment of the invention can have relatively high purities of at least about 90%, preferably at least about 95%, and up to about 97% and higher. Further, increased purities can be obtained at this stage with minimal loss of percent recovery, i.e., at least about 45%, preferably at least about 55%, and more preferably at least about 65% recovery. Recoveries can be improved by recovering DMBB from the portion of the slurry removed prior to centrifugation and/or from the wash and/or mother liquors used in centrifugation.

Figure 2:
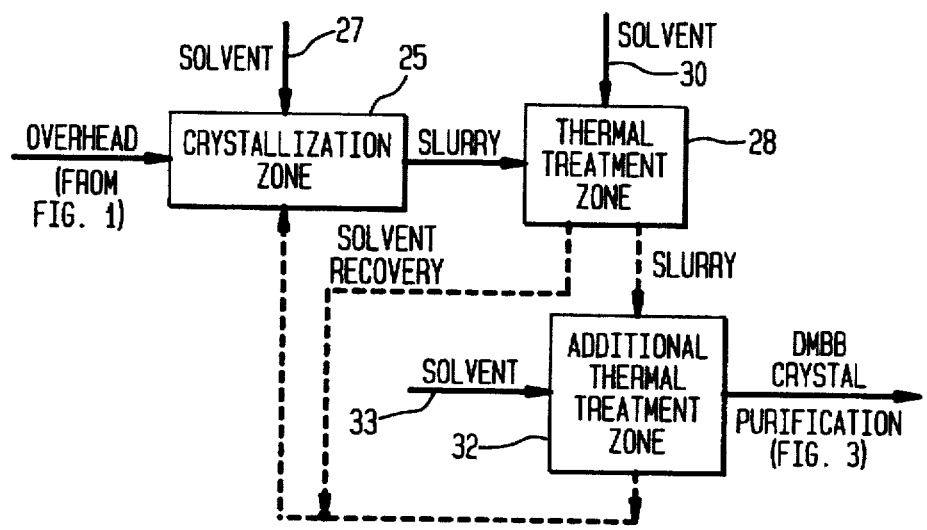
FIG. 2 is a flow chart illustrating a process for continuously crystallizing DMBB from byproduct streams of DMT production.

In yet another embodiment of the invention, overhead product stream 20 of FIG. 1 is directed to a conventional condenser (not illustrated), and the condensate is then subjected to a "continuous" DMBB crystallization and concentration process, as shown in FIG. 2.

Turning to FIG. 2, overhead condensate (temperature from about 70° C. to about 100° C.) is directed to a crystallizer 25, within which DMBB is precipitated or crystallized. The overhead product stream 20 is added to organic solvent 27 having a first temperature which is at or below the temperature at which DMBB begins to precipitate in that solvent system, so that DMBB precipitates substantially immediately upon addition of the overhead to the solvent. In effect, DMBB present in the overhead is substantially immediately precipitated or "crashed" out of solution upon addition of the overhead to the solvent. Such "immediate precipitation" can begin as quickly as 0 to 30 minutes after overhead is added to solvent, and typically DMBB crystallization is completed within 0 to 15 minutes after addition of overhead. The organic solvent can be any organic solvent as described above, preferably a lower alkanol, more preferably methanol.

As the skilled artisan will appreciate, DMBB precipitation temperatures can vary depending upon the solvent used, the concentration of the various organic compounds in the overhead stream, the temperature of the overhead, and the like. In an especially preferred embodiment of the invention, the organic solvent is methanol, and the temperature of the methanol is selected so as to provide a DMBB precipitation temperature of about 20° C. to about 30° C., more preferably about 25° C.

The amount of solvent can vary, ranging from about 0.5 to about 2.0 times the weight of condensate, and preferably about 1 times the weight of condensate (i.e., organic solvent and overhead condensate are mixed in substantially equal weight quantities). Higher and/or lower quantities of overhead and/or organic solvent can be used, but as the skilled artisan will appreciate, too much or too little can result in loss of material, decreased purity of the recovered product, and the like.

Processing times can be greatly improved in accordance with the present invention by reducing the total volume of liquid present in the slurry prior to subsequent processing. To minimize loss of crystallized DMBB, the solid components of the slurry (i.e. DMBB crystals) can be allowed to settle, typically over a period of about 30 to 45 minutes. The total volume of the liquid portion of the slurry can then be effectively reduced by removing a portion of the liquid thereof (which includes the organic solvent, as well as other organic compounds dissolved therein) with minimal loss of DMBB crystals. The liquid volume of the slurry can be reduced about 10 percent, for example by pressure decantation, and the solvent thus removed routed to a suitable solvent recovery zone and/or rerouted into subsequent processing steps as described below. The amount of solvent removed can be monitored using suitable liquid level indicators or controls as known in the art to prevent substantial loss of the crystallized product.

After DMBB precipitation, the resultant slurry is directed to thermal treatment zone 28 where the slurry is thermally treated to increase the concentration and purity of the DMBB crystals. In this regard, typically organic compounds other than DMBB are also present in the overhead product and can also precipitate during DMBB precipitation. This is particularly true when the DMBB is rapidly crashed out of the overhead at low temperatures.

Preferably, the slurry is treated within zone 28 at a second temperature which is greater than the DMBB precipitation temperature to solubilize any other organic crystals without solubilizing the DMBB crystals. Thus, although initial impurities may be present in the slurry, DMBB crystal concentration can be maximized in the initial precipitation stage, and impurities thereafter effectively reduced or minimized by thermal treatment.

In an especially preferred embodiment of the invention, the slurry is thermally treated with solvent in a vessel separate from crystallizer 25. The solvent in thermal treatment zone 28 can include solvent which was removed from crystallization zone 25 and thereafter directed to thermal treatment zone 28, solvent from a separate source (as indicated by 30), solvent from downstream processing described below, and/or combinations of any of these sources.

Treatment conditions, such as the amount of and temperature of the solvent, are selected to minimize loss of the desired DMBB product and impurities of the product. For example, for methanol, the temperature of the solvent preferably is about 30° C. to about 45° C. and the ratio of methanol to DMBB crystals can range from about 0.5:1 to about 5:1.

Processing times at this stage can also be greatly improved by reducing the total volume of liquid present in the slurry prior to subsequent processing, as described above. To minimize loss of crystallized DMBB, the solid components of the slurry (i.e. DMBB crystals) can be allowed to settle, again typically over a period of about 30 to 45 minutes. The liquid volume of the slurry can be reduced by about 10 percent to about 30 percent, for example by pressure decantation, and the solvent thus removed routed to a suitable solvent recovery zone and/or rerouted into other processing steps (such as other thermal treatment steps and/or crystallization step). The amount of solvent removed can be monitored as described above.

The thermally treated slurry of DMBB crystals can be subjected to a series of additional thermal treatment steps, each of which is conducted at a higher temperature than the last, preferably also in separate vessels. For example, in a preferred embodiment of the invention, the slurry is directed to at least one additional thermal treatment zone 32, in which the slurry is treated with solvent at a temperature of about 45° C. to about 55° C. The solvent in thermal treatment zone 32 can include solvent which was removed from crystallization zone 25 and/or thermal treatment zone 28 and thereafter directed to thermal treatment zone 32, solvent from a separate source (as indicated by 33), solvent from additional downstream processing and/or combinations of any of these sources.

Again processing times at this stage can also be improved by reducing the total volume of liquid present in the slurry, for example, by allowing the slurry solids to settle (again typically over a period of about 30 to 45 minutes) and reducing the total volume of the liquid portion of the slurry by about 10 percent to about 40 percent, for example by pressure decantation. The solvent thus removed can be directed to a suitable solvent recovery zone and/or rerouted into other processing steps (such as other thermal treatment steps and/or crystallization step).

Thermal treatment temperatures should not exceed the temperature at which DMBB is solubilized in the organic solvent, so as to minimize loss of DMBB product.

Because the overhead is added to the solvent to provide rapid precipitation of DMBB, time consuming DMBB crystallization conditions, including overhead solubilization and cooling, are not required. This can result in substantial time savings in the DMBB recovery process. Although precipitation occurs rapidly and with minimal control of crystallization conditions, it is currently believed that the recovered DMBB crystals can have relatively high purities of at least about 90%, preferably at least about 95%, and up to about 97% and higher as determined using gas chromatographic analysis. Increased purities are also believed to be obtainable with minimal loss of percent recovery at this crystallization stage.

This embodiment of the invention can also provide benefits in solvent recovery. In this regard, as described above and as illustrated at FIG. 2, solvent can be removed from any of the crystallization and/or thermal treatment steps. The recovered solvent can be disposed of, or, as indicated by the broken lines of FIG. 2, directed to additional downstream processing and recycled for use in processing additional batches of the DMT byproduct stream. For example, solvent can be recovered from thermal treatment zone 28 and directed back into crystallization zone 25. Solvent can also be recovered from any additional thermal treatment zones, such as zone 32, and also directed into crystallization zone 25.

The DMBB crystals recovered from a DMT production byproduct stream using any of the crystallization techniques described above (crash, solvent reduction or continuous) can be further purified in subsequent recrystallization steps, for example, to a purity of greater than 99.8%, approaching 99.9% and greater. For the continuous crystallization aspect of the invention, the DMBB crystals can be recrystallized and purified without time consuming crystal recovery steps (for example, using centrifugation). Thus, continuous crystallization can provide improved processing times and efficiencies in this regard as well.

Figure 3:
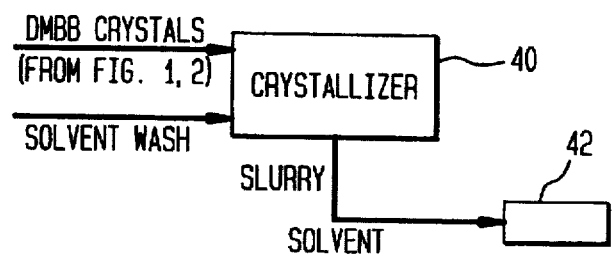
FIG. 3 is a flow chart illustrating a process for recrystallizing DMBB recovered using the processes illustrated in FIGS. 1 and 2.

Turning now to FIG. 3, a flow diagram illustrating an exemplary recrystallization schematic for further purifying DMBB is shown. DMBB crystals recovered from a DMT production byproduct stream, for example as described above with reference to FIGS. 1 or 2, are fed to an appropriate crystallization vessel 40 as known in the art. An organic solvent, which may be the same or different as the organic solvents described above, is also directed to crystallization vessel 40.

The DMBB crystals and organic solvent are subjected to conditions sufficient to form a solution of the DMBB crystals in the organic solvent, for example, by heating the slurry of DMBB crystals and solvent in the crystallization vessel 40. The slurry can be heated to temperatures ranging from about 150° C. to about 165° C., and advantageously is at least about 150° C. to about 155° C., although higher or lower temperatures can be used. For example, as the skilled artisan will appreciate, higher temperatures can be used for increased loading of DMBB crystals into solution.

The residence time at the solubility temperature in this aspect of the invention can vary, ranging from about 45 minutes to about 90 minutes, and preferably is about 60 minutes. Residence time should be sufficiently long to allow DMBB crystals to dissolve in the organic solvent, but should not be so long such that higher molecular weight compounds begin to decompose, and thus adversely affect purity of the resultant product.

The ratio of DMBB crystals to organic solvent added to crystallizer 40 can vary, depending upon the composition of the DMBB crystals. Generally, the composition in crystallizer 40 should range from about 0.05 to about 0.40 part DMBB per part organic solvent, although lower or higher DMBB concentrations are possible depending upon the level of impurities in the DMBB crystals.

After the solution is formed, the solution is then subjected to controlled cooling rate conditions to initiate precipitation and crystallization of purified DMBB crystals. Preferably the solution is cooled while controlling the rate of cooling during at least two cooling stages. The solution can be cooled in a first controlled cooling stage from the initial solubilizing temperature (i.e., from about 150° C. to 155° C.) to a temperature at which DMBB crystallization is substantially complete (i.e., for methanol about 135° C.). The solution is then cooled during a second controlled cooling stage from a temperature at which DMBB crystallization is substantially complete to the desired filtration temperature, i.e., that temperature at which cooling is ceased to prevent crystallization of undesired contaminants and/or maximum crystallization is achieved of DMBB. For methanol solvent, the solution is cooled in the second cooling stage from a temperature of about 135° C. to a filtration temperature of about 50° C. to 60° C.

Preferably, the solution is cooled during the first cooling stage at a rate selected to maximize DMBB crystallization and also to minimize crystallization of impurities, preferably at a rate of less than or about 0.05° C. to about 0.2° C. per minute, and more preferably less than or about 0.15° C. per minute. The solution is thereafter preferably cooled during the second cooling stage at a rate of less than or about 0.5° C. to about 2.0° C. per minute, and preferably less than or about 1.0° C. per minute until the target filtration temperature is reached. The controlled cooling rates are advantageous in that the desired end product, DMBB, can be selectively recrystallized, while maintaining undesired contaminants in solution.

As noted above, the solution is cooled to a target filtration temperature, for example, about 50° C. to 60° C., preferably about 55° C., for methanol solvent systems. Lower and/or higher filtration temperatures can be used depending upon the composition of the DMBB crystals fed to crystallizer 40. For example, for DMBB crystals having relatively low DMT concentrations, i.e., less than about 0.5%, lower filtration temperatures can be used. However, lower filtration temperatures can adversely affect yield and purity percentages for DMBB crystals having higher DMT concentrations.

After reaching the filtration temperature, the resultant slurry which includes suspended DMBB crystals is directed to a conventional filter and dryer apparatus, designated generally in FIG. 3 as 42, and the slurry is washed with additional organic solvent, preferably the same as the solvent used in the crystallizer 40. The wash temperature of the wash liquor preferably is the same as the target filtration temperature to achieve maximum recovery and purity yields. For methanol washes, wash temperature advantageously is about 50° C. to about 60° C., and preferably about 55° C. The filtered and dried DMBB crystals are then recovered. As indicated in FIG. 3, the wash liquor can also be recovered and directed to conventional recovery and/or disposal means.

As noted above, the recrystallization process illustrated in FIG. 3 is advantageous for providing DMBB having a purity at least about 99.8% and higher, and purities of 99.9% have been achieved. In addition, the recovery of DMBB in this recrystallization stage can be at least about 90%, and more preferably at least about or greater than 95%.

DMBB crystals recovered using the rapid crystallization embodiment of the invention can be obtained in overall yields (distillation, rapid crystallization and recrystallization) of at least about 25%, preferably at least about 30%, and more preferably at least about 40% overall recovery.

DMBB crystals recovered using the solvent reduction embodiment of the invention can be obtained in overall yields (distillation, crystallization, solvent reduction and recrystallization) of at least about 25%, preferably at least about 40%, and more preferably at least about 50%.

DMBB crystals recovered using the continuous crystallization embodiment of the invention can be obtained in overall yields (distillation, continuous crystallization and recrystallization) of at least about 25%, preferably at least about 40%, and higher.

Figure 4:
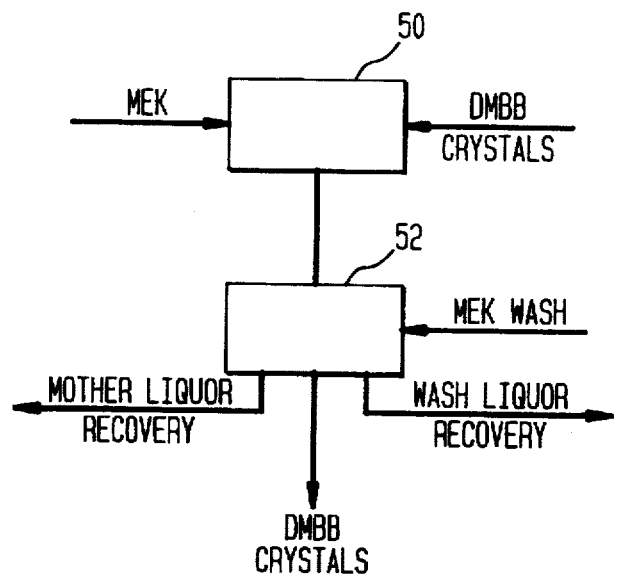
FIG. 4 is a flow chart illustrating a process for further purifying DMBB recovered in accordance with the various embodiments of the invention.
Figure 5:
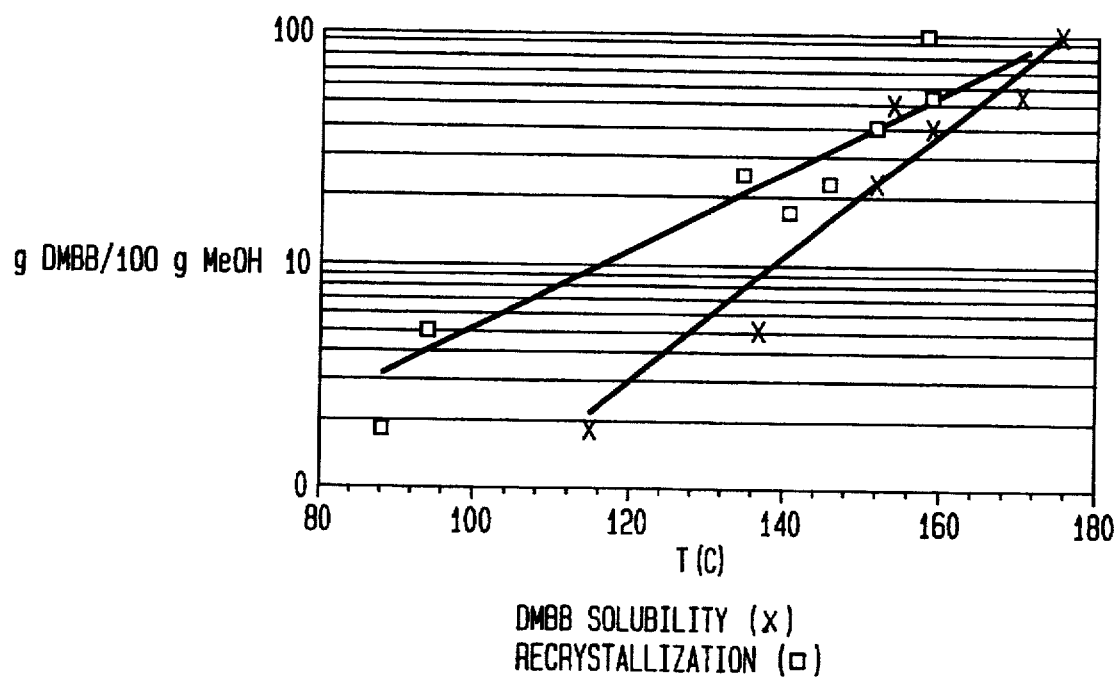
FIG. 5 is a graph illustrating DMBB solubility and recrystallization behavior in methanol.

In yet another aspect of the present invention, 4,4'-dicarbomethoxybenzophenone (DCMB) can be removed from DMBB crystals recovered from DMT production byproduct streams. Turning now to FIG. 4, DMBB crystals, recovered for example from the process described in FIG. 3, are charged to a crystallizer 50. An organic solvent suitable for DMBB recrystallization at generally atmospheric conditions (without temperatures substantially above the solvent boiling point) is also charged to crystallizer 50 to suspend the DMBB crystals and to form a slurry. Preferred solvents include aliphatic ketones, such as methyl ethyl ketone (MEK), methyl isobutyl ketone (MIBK), and the like, and amides such as dimethylacetamide (DMAc), dimethylformamide (DMF), and the like. The ratio of DMBB crystals and solvent within crystallizer 50 can impact this purification step, for example, for MEK, the slurry includes 3% or less DMBB.

The slurry is heated to dissolve the DMBB crystals into the MEK solvent, preferably heated to the boiling point of the solvent (for example, for MEK, 80° C.) and held for about 1 hour to ensure complete dissolution of DMBB within the solvent. The resultant solution is thereafter cooled to a temperature sufficient to initiate precipitation or crystallization of DMBB from solution, preferably to a temperature of about 35° C. (for MEK).

The recrystallized DMBB slurry can be transferred to an appropriate filter 52 wherein the DMBB crystals are washed with additional solvent (which may be the same or different, preferably the same) and thereafter dried. The resultant DMBB crystals are recovered as are the wash liquor and mother liquors, each of which are directed to appropriate recovery zones.

The recovered DMBB crystals can exhibit exceptionally high purity, of greater than 99.9%. Recovery of DMBB in this additional purification step can be as high as 65%, and preferably as high as 70% and higher. It is to be noted that the recrystallization is successful for DMBB crystals having less than or about 3% DCMB contamination (for MEK). For DMBB feed streams having greater than about 3% DCMB contamination (using MEK as the solvent), recrystallization can be increasingly difficult. As the skilled artisan will appreciate, filtration temperatures, boiling points, DMBB and DCMB concentrations, and the like, can vary for different solvent systems.

The following examples further illustrate the invention.

DMT BYPRODUCT STREAM DISTILLATION

Distillation Example 1

121.9 kg/hr of DMT residue was pumped through a strainer and into a vacuum flasher operating at 240° C. and 20 mm Hg. The flasher process achieved a 1.5/98.5 overhead:bottoms split. The resulting 120.1 kg/hr of flasher bottoms were pumped to a thin film evaporator (TFE) operating at 278° C. and 14.5 mm Hg. TFE process achieved a 27.6/72.4 overhead:bottoms split. The TFE overhead vapors were condensed. The condensate containing 4.1% DMBB, 11.0% DMT, and 9.5% benzyl esters/biphenyls was stored at 100° C. in a vessel for subsequent crystallization recovery. Recovery of DMBB at the flasher was 97%, and recovery of DMBB at TFE was 65%. The continuous distillation process recovery was 63% overall.

Distillation Example 2

130.5 kg/hr of DMT residue was pumped through a strainer and into a vacuum flasher operating at 240° C. and 30 mm Hg. The flasher process achieved a 3.4/96.6 overhead:bottoms split. The resulting 126.1 kg/hr of flasher bottoms were pumped to a thin film evaporator (TFE) operating at 279° C. and 10.6 mm Hg. TFE process achieved a 47/53 overhead:bottoms split. The overhead vapors were condensed. The condensate containing 3.4% DMBB, 7.7% DMT, and 13.9% benzyl esters/biphenyls was stored at 100° C. in a vessel for subsequent crystallization recovery. Recovery of DMBB at the flasher was 94%, and recovery of DMBB at TFE was 94%. The continuous distillation process recovery was 88% overall.

Distillation Example 3

121.1 kg/hr of DMT residue was pumped through a strainer and into a vacuum flasher operating at 240° C. and 40 mm Hg. The flasher process achieved a 0.3/99.7 overhead:bottoms split. The resulting 120.8 kg/hr of flasher bottoms were pumped to a thin film evaporator (TFE) operating at 270° C. and 16.5 mm Hg. TFE process achieved a 36/64 overhead:bottoms split. The overhead vapors were condensed. The condensate containing 6.6% DMBB, and 1.5% DMT, and 0.35% benzyl esters/biphenyls was stored at 100° C. in a vessel for subsequent crystallization recovery. Recovery of DMBB at the flasher was 99% and recovery of DMBB at TFE was 79%. The continuous distillation process recovery was 79% overall.

As shown by examples above, distillation overhead/bottom splits ranging from 28:72–47:53 produced overall distillation stage recoveries ranging from 63–88%. Additional downstream processes yield high DMBB purities (>99.8%) with high overall recoveries, as demonstrated by the following examples.

The distillation examples illustrate that improved yields can be achieved in accordance with the invention by including heavier molecular weight compounds in the overhead split. For example, for DMT residue streams comprising less than about 10% DMT (Distillation Examples 2 and 3), distillation is controlled to provide overhead:bottom splits ranging from about 35:65 to about 50:50 so that heavier compounds are included in the overhead split. In contrast, examples 1 and 2 of DE 4312491 (illustrating distillation prior to crystallization) describe 20:80 to 36:64 overhead:bottom splits for similar feedstream DMT levels (less than about 10% DMT). Accordingly, minimal or no heavy compounds were included in the overhead split, and the overall yields reported in these examples were less (about 25%).

Distillation Example 1 above illustrates about a 30:70 overhead:bottom split for a feedstream having greater than about 10% DMT. Including heavier compounds in the overhead resulted in improved DMBB recoveries and purities downstream, despite the relatively high level DMT content initially. DE 4312491 does not demonstrate recovery of DMBB from DMT byproduct streams having relatively high levels of DMT (greater than about 10% DMT).

The distillation overhead/bottom splits are achieved at extremely high temperatures for such low pressures. The DE 4312491 patent does not recognize the role of the content of higher molecular weight organic compounds (benzyl esters and biphenyls) in the overhead in solubilizing the impurities during crystallization.

DMBB RAPID CRYSTALLIZATION

DMT byproduct streams having varying concentrations of DMBB and DMT were distilled and the overhead treated to rapidly crystallize DMBB in accordance with one embodiment of the invention. The following examples illustrate crystallization conditions for the rapid crystallization process of the present invention, as well as crystallization conditions using a cooling curve (comparative).

DMBB Rapid Crystallization Example 1 (Invention)

In a crystallizer vessel, approximately 250 Kg of methanol was charged and heated to 45° C., the filtration temperature. To the methanol was added all at once 250 Kg of overhead containing 10.0% dimethyl terephthalate and 3.2% 4,4'-dimethyl bibenzoate (DMBB). The resulting slurry was centrifuged immediately and washed with 20 parts of room temperature methanol to 1 part of solid, dried for 90 minutes in the centrifuge, weighed and analyzed by gas chromatography.

There was a significant time savings using the crash crystallization technique of the invention in comparison to the standard cooling curve crystallization of Example 3 below. This process resulted in 47.7% crystallization recovery (38.8% overall recovery from DMT distillate stream) of DMBB with 98.6% purity. This process produced a significant increase in purity using the overhead composition described above in comparison to the purity reported in the standard cooling curve crystallization in Example 3 below (comparative). This process also produce an increase in the overall recovery (38.8% overall) from the DMT distillate in comparison to the overall recovery of 25% reported in the DE 4312491.

DMBB Rapid Crystallization Example 2 (Invention)

In a crystallizer vessel, approximately 250 Kg of methanol was charged and heated to 40° C., the filtration temperature. To the methanol was added all at once 250 Kg of overhead containing 9.1% dimethyl terephthalate and 3.3% 4,4'-dimethyl bibenzoate (DMBB). The resulting slurry was centrifuged immediately and washed with 20 parts of room temperature methanol to 1 part of solid and dried for 90 minutes in the centrifuge, weighed and analyzed by gas chromatography.

There was a significant time savings using the crash crystallization technique in comparison to the standard cooling curve crystallization in Example 3 below. This process resulting in 64.7% crystallization recovery (52.0% overall recovery from DMT distillate stream) of DMBB with 97.6% purity. This process produced a significant increase in purity using the overhead composition described above in comparison to the purity reported in the standard cooling curve crystallization in Comparative Example 3. This process also produce an increase in the overall recovery from the DMT distillate in comparison to the overall recovery of 25% reported in the DE 4312491.

DMBB Crystallization Example 3 (Comparative)

In a crystallizer vessel, approximately 250 Kg of methanol was charged and heated to just below the boiling point, 65° C. To the methanol was added 250 Kg of overhead containing 8.6% dimethyl terephthalate (DMT) and 3.8% 4,4'-dimethyl bibenzoate (DMBB). The resulting solution was cooled using a programmed cooling curve for 120 minutes to the filtration temperature, 50° C. The cooled solution was centrifuged and washed with 20 parts of room temperature methanol to 1 part solid and dried for 90 minutes, weighed and analyzed by gas chromatography. This cooling curve crystallization process resulted in 73.2% recovery (58.8% overall recovery from DMT distillate stream) of DMBB with 90.8% purity.

The foregoing DMBB crystallization examples illustrate the advantages of the rapid crystallization techniques of the invention with regard to time savings and purity, particularly in comparison to those exhibited using DMBB cooling curves to crystallize DMBB and to that reported in DE 4312491.

DMBB CRYSTALLIZATION/SOLVENT REDUCTION

DMT byproduct streams were distilled as described above and the overhead treated to crystallize DMBB. Crystal recovery conditions in accordance with the solvent reduction embodiment of the invention, and in accordance with comparative crystallization techniques, are given in Crystallization/Solvent Reduction Examples 1 and and the comparative Example 2 below, respectively.

DMBB Crystallization/Solvent Reduction Example 1 (Invention)

In a crystallizer vessel, approximately 375 Kg of methanol was charged and heated to just below the boiling point, 65° C. To the methanol was added 250 Kg of overhead containing 9.61% dimethyl terephthalate (DMT) and 3.28% 4,4'-dimethyl bibenzoate (DMBB). The resulting solution was cooled using a programmed cooling curve for 120 minutes to the filtration temperature, 45° C.

The resulting solution was held for 30 minutes without stirring at 45° C. to settle the solids and decanted using positive pressure. Approximately 31% of the solution was removed and the resulting concentration slurry was centrifuged in half the time as compared to standard cooling curve crystallization detailed in Comparative Crystallization Example 2 (below). The solids were washed with 20 parts of methanol to 1 part of solids and dried for 90 minutes, weighed and analyzed by gas chromatography.

This process resulted in 75.9% crystallization recovery (61% overall recovery from DMT distillate stream) of DMBB with 98.1% purity. This process produced a significant increase in purity using overhead composition as described above in comparison to the purity reported to the standard cooling curve crystallization in Example 2. This process also produce an increase in the overall recovery from the DMT distillate in comparison to the overall recovery of 25% reported in DE 4312491.

DMBB Crystallization Example 2 (Comparative)

In a crystallizer vessel, approximately 250 Kg of methanol was charged and heated to just below the boiling point, 65° C. To the methanol was added 250 Kg of overhead containing 8.6% dimethyl terephthalate (DMT) and 3.8% 4,4'-dimethyl bibenzoate (DMBB). The resulting solution was cooled using a programmed cooling curve for 120 minutes to the filtration temperature, 50° C. The cooled solution was centrifuged and washed with 20 parts of room temperature methanol to 1 part solid and dried for 90 minutes, weighed and analyzed by gas chromatography. This standard cooling curve crystallization process resulted in 73.2% recovery (58.8% overall recovery from DMT distillate stream) of DMBB with 90.8% purity.

DMBB CONTINUOUS CRYSTALLIZATION

DMT byproduct streams were distilled as described above and the overhead treated to continuously crystallize DMBB. Crystallization conditions of the continuous crystallization embodiment of the invention and of a comparative example using a controlled cooling curve are given below.

DMBB Continuous Crystallization Example 1 (Invention)

In a first crystallization zone, approximately 250 Kg of methanol is charged and heated to 25–35° C. To the methanol is added 250 Kg of overhead containing approximately 8–10% dimethyl terephthalate (DMT) and 3–4% 4,4'-dimethyl bibenzoate (DMBB). The resulting solution is cooled to 25–35° C. due to the temperature rise from the addition of 70–100° C. overhead. Since there is minimal stirring, the solids will settle and this concentrated slurry is transferred from the first crystallization zone into a second crystallization zone which contains additional methanol heated to 35–45° C. sufficient to maintain a 1:1 ratio of solids to liquid. Some of the impurities solubilize and the remaining DMBB and reduced impurities settle and are transferred to a third crystallization zone. This zone contains additional methanol heated to 55° C. sufficient to maintain a 1:1 ratio of solids to liquid. Only DMBB remains crystalline and this concentrated slurry is transferred to a recrystallization zone for further purification. Since centrifugation is necessary and this is a continuous process, there is a substantial time savings in comparison to the standard batch crystallization process in Example 2.

DMBB Crystallization Example 2 (Comparative)

In a crystallizer vessel, approximately 250 Kg of methanol was charged and heated to just below the boiling point, 65° C. To the methanol was added 250 Kg of overhead containing 12.1% dimethyl terephthalate (DMT) and 3.7% 4,4'-dimethyl bibenzoate (DMBB). The resulting solution was cooled using a programmed cooling curve for 120 minutes to the filtration temperature, 50° C. The cooled solution was centrifuged and washed with 20 parts of room temperature methanol to 1 part solid and dried for 90 minutes, weighed and analyzed by gas chromatography. This cooling curve crystallization process resulted in 67.6% recovery (54.3% overall recovery from DMT distillate stream) of DMBB with 85.8% purity.

DMBB RECRYSTALLIZATION

DMBB Recrystallization Example 1

Crude DMBB was combined with methanol in a 10 gallon reactor, and various concentrations of DMBB and impurities were obtained. The mixtures were heated from room temperature to 155° C. The residence time at solubility set point was greater than or about 60 minutes. Afterwards, the reactor contents were cooled down from 155–135° C. at 0.1–0.15° C./min and from 135° C. to a filtration temperature of 50–60° C. at a rate of 0.6–0.9° C./min. Recovered crystals were washed twice with greater than or about 5.0 Kg methanol/kg dry cake at the same filtration temperature and dried under 0.5 psia vacuum at 50° C. internal. Initial concentration of representative batches and the resulting DMBB purities and recoveries are set forth in the Table below.

| Batch | kg DMBB kg MeOH feed | kg DMT kg MeOH feed | kg DCMB kg MeOH fee | kg isomer kg MeOH feed | Purity % | Recovery % |
|---|---|---|---|---|---|---|
| 1 | 0.17 | 0.0013 | 0.0032 | 0.0022 | 99.8 | 74 |
| 2 | 0.18 | 0.0160 | 0.0000 | 0.0022 | 99.8 | 99 |
| 3 | 0.34 | 0.0681 | 0.0026 | 0.0015 | 99.8 | 90 |

Note: Concentrations for Batch 2 and 3 are weighted averages of combined batches of crude DMBB.

Nineteen pilot scale batches were performed near to or at the above operating conditions with concentration ranges from 0.2 to 0.3 kg DMBB/kg methanol. Eleven of these produced >99.8% purity product while 5 of these had purities between 99.8% and 99.6%. The average recovery for all batches was >95%.

DMBB Recrystallization Example 2

In a small bench-scaled viewcell, 13 g of methanol was combined with 2.96 g of crude DMBB. The concentration of the mixture was 0.23 kg DMBB/kg MeOH, 0.0016 kg DMT/kg MeOH, 0.0039 kg DCMB/kg MeOH, 0.0027 kg isomer/kg methanol. The mixture was heated from room temperature to 152° C. and 184 psig and held at those conditions for 62 minutes for complete solubility to be obtained. At a temperature of 146° C., precipitation began. Complete precipitation lasted for 5 minutes.

DMBB Recrystallization Example 3

The DMBB solubility and recrystallization behavior in methanol was studied using a viewcell apparatus. Approximately thirteen runs were done. Ten tests were performed with synthetically produced 99.9% DMBB and three tests were performed with 91% DMBB recovered by DMT residues.

FIG. 4 is a graph showing regression analyses of the data with correlation coefficients >95%. Equations to the curves are $\log[S]=0.0274[T_S]-2.8$ and $\log[R]=0.0174[T_R]-1.03$, where S and R represent the pure DMBB content in methanol at solubility and recrystallization respectively in units of g DMBB/100 g MeOH. $T_S$ and $T_R$ are the onset solubility and recrystallization temperatures in units of ° C. The time required for completing solubility ranged from 55 min at 115° C. to 20 min at 175° C. The corresponding times to complete recrystallization ranged from 25° C. to 65° C. to 8 min at 158° C. System pressures matched the vapor pressure of methanol.

REWORK OF DMBB CRYSTALS WITH DCMB CONTAMINATION

Rework of DMBB Crystals with Methyl Ethyl Ketone (MEK)

In a round bottom flask, methyl ethyl ketone (MEK) was added to impure 4,4'-dimethyl bibenzoate (DMBB) containing approximately 3.5% of 4,4'dicarbomethoxy benzophenone (DCMB). A ratio of 1 part of impure DMBB to 50 parts of MEK was maintained. The resulting solution was heated to the boiling point of MEK, 80° C., while stirring and the solution was allowed to reflux for 1 hour. The solution was then cooled to 38° C. and filtered. The resulting solids were dried and analyzed by gas chromatography. This recrystallization yielded 79% recovery with >99.9% DMBB.

Rework of DMBB Crystals with Dimethyl Acetamide (DMAc)

In a round bottom flask, dimethyl acetamide (DMAC) was added to impure 4,4'-dimethyl bibenzoate (DMBB) containing approximately 3.5% of 4,4'dicarbomethoxy benzophenone (DCMB). A ratio of 1 part of impure DMBB to 22 parts of DMAc was maintained. The resulting solution was heated to the boiling point of DMAC, 100° C., while stirring and the solution was allowed to reflux for 1 hour. The solution was then cooled to room temperature and filtered. The resulting solids were dried and analyzed by gas chromatography. This recrystallization yielded 87% recovery with >99.9% DMBB.

Rework of DMBB Crystals with Methyl Isobutyl Ketone (MIBK)

In a round bottom flask, methyl isobutyl ketone (MIBK) was added to impure 4,4'-dimethyl bibenzoate (DMBB) containing approximately 3.5% of 4,4'-dicarbomethoxy benzophenone (DCMB). A ratio of 1 part of impure DMBB to 30 parts of MIBK was maintained. The resulting solution was heated to the boiling point of MIBK, 118° C., while stirring and the solution was allowed to reflux for 1 hour. The solution was then cooled to 55° C. and filtered. The resulting solids were dried and analyzed by gas chromatography. This recrystallization yielded 85% recovery with >99.9% DMBB.

POLYMERIZATION OF RECOVERED DMBB

DMBB can be recovered from DMT residues in accordance with the process of the present invention to consistently produce a monomer with a low acid, low hazen, and low ash content. A low acid content is necessary for production efficiency. Low hazen is ideal for aesthetic customer appeal. No to low ash content is essential for polymer and film markets of the electronic industry.

Generally, synthetically produced DMBB has residual acid left from catalyst removal steps. The resulting high acid values cause long transesterification times during polycondensations and the increased times promote degradative yellowing of the polymer.

Analyticals on the recovered monomer according to the process described in DE 4312491 were not reported. However, acid numbers determined from in-house studies indicate monomer could be problematic for commercial scale production efficiency.

The present invention can provide for the production of DMBB with low acid, low hazen, and low ash content. This is because no acid washes are needed for catalyst removal as in the case for synthetic process. Low hazen number are possible given favorable temperature and pressure conditions during distillation. The condensed distillate selected as the crystallization feed excludes the introduction of the ash materials, which are non-volatile.

The present application provides a process for consistently recovering DMBB from DMT byproduct streams having greater than 99.8% DMBB purity and greater than 25% DMBB recovery overall. As discussed above, in accordance with the present invention, a volatile residue can be distilled under low pressures, and the condensate can be combined with a solvent to rapidly crystallize the DMBB product, resulting in improved process times, with good purity and recovery. The recovered DMBB can be recrystallized under pressure using a solvent that has low DMBB solubility at atmospheric conditions. The resulting DMBB product can be produced in both high purities and high overall recoveries.

These results are not limited by the feed variability inherent to the DMT residue stream. Feedstream distillation can result in a balanced DMT, benzyl ester, and biphenyl content in the crystallizer feed so that the advantageous purities and recoveries can be achieved consistently, as exemplified by the foregoing examples.

The foregoing examples are illustrative of the present invention and are not to be construed as limiting thereof. The invention is defined by the following claims, with equivalents to the claims to included therein.

That which is claimed is:

1. A process for recovering 4,4'-dimethyl bibenzoate (DMBB) from a byproduct stream from dimethyl terephthalate (DMT) production, comprising:

separating DMBB from a byproduct stream of dimethyl terephthalate (DMT) production comprising DMT and DMBB in a first concentration to provide a DMBB concentrate stream comprising DMBB in a higher concentration than said first concentration; and adding said DMBB concentrate stream to an organic solvent under conditions sufficient to form a suspension of crystallized DMBB in said organic solvent substantially immediately upon addition of the DMBB concentrate stream to the solvent.

2. The process of claim 1, wherein the step of adding said DMBB concentrate stream to the organic solvent comprises adding substantially equal weight amounts of said DMBB concentrate stream to the solvent.

3. The process of claim 1, wherein the step of adding said DMBB concentrate stream to the organic solvent comprises adding said DMBB concentrate stream to organic solvent having a temperature at or below the temperature at which DMBB precipitates in said solvent.

4. The process of claim 1, wherein said organic solvent is an alkanol having 1 to 8 carbon atoms.

5. The process of claim 4, wherein said organic solvent is methanol.

6. The process of claim 5, wherein said DMBB concentrate stream has a temperature of about 70° C. to about 100° C. and wherein said methanol has a temperature of about 40° C. to about 50° C.

7. A process for recovering 4,4'-dimethyl bibenzoate (DMBB) from a byproduct stream of dimethyl terephthalate (DMT) production, comprising:

separating DMBB from a byproduct stream of dimethyl terephthalate (DMT) production comprising DMT and DMBB in a first concentration to provide a DMBB concentrate stream comprising DMBB in a higher concentration than said first concentration;

forming a solution of said DMBB concentrate stream with an organic solvent;

cooling said solution to form a suspension of crystallized DMBB in said organic solvent;

removing at least a portion of the organic solvent from said suspension; and centrifuging said suspension to recover said crystallized DMBB from the remaining portion of said organic solvent.

8. The process of claim 7, wherein said treating step comprises distilling said byproduct stream.

9. The process of claim 7, wherein said solution forming step comprises adding organic solvent to said DMBB concentrate stream in an amount ranging from about 0.5 to about 2.5 times the weight of said DMBB concentrate stream.

10. The process of claim 9, wherein said organic solvent is methanol.

11. The process of claim 7, wherein said removing step comprises removing at least about 25 to about 40 percent of the total volume of said organic solvent from said suspension.

12. A process for recovering 4,4'-dimethyl bibenzoate (DMBB) from a byproduct stream of dimethyl terephthalate (DMT) production, comprising:

distilling a byproduct stream from DMT production comprising DMBB and DMT to produce an overhead stream that includes DMBB;

forming a solution of said overhead stream with an organic solvent;

cooling said solution to form a suspension of crystallized DMBB in said organic solvent;

reducing the volume of the organic solvent of said suspension;

centrifuging said suspension to separate said crystallized DMBB from the remaining volume of said organic solvent; and sequentially repeating said distilling, forming, cooling, reducing and centrifuging steps with different DMT byproduct stream charges, wherein said centrifuging step is conducted such that the throughput of said suspension of DMBB crystals through said centrifuge is at least 2 times faster than without said volume reducing step.

13. A process for recovering 4,4'-dimethyl bibenzoate (DMBB) from a byproduct stream from dimethyl terephthalate (DMT) production, comprising:

distilling a byproduct stream of dimethyl terephthalate (DMT) production comprising DMT and DMBB in a first concentration to provide an overhead stream comprising DMBB in a concentration higher than said first concentration;

adding said overhead stream to an organic solvent having a first temperature which is at or below the temperature at which DMBB precipitates in said organic solvent to form a suspension of DMBB crystals in said solvent substantially immediately upon addition of the overhead stream to the solvent; and thermally treating said suspension at a second temperature greater than said first temperature to increase the concentration of DMBB crystals of said suspension.

14. The process of claim 13, further comprising after said thermally treating step thermally treating said suspension at a temperature greater than said second temperature to further increase the concentration of DMBB crystals of said suspension.

15. The process of claim 13, wherein:

said adding step comprises adding said overhead to methanol at a first temperature of about 20° C. to about 30° C.; and said thermally treating step comprises adding said suspension to methanol at a second temperature of about 30° C. to about 45° C.

16. The process of claim 13, further comprising recovering at least a portion of said organic solvent from said suspension prior to said thermal treatment step.

17. The process of claim 16, further comprising:

recovering at least a portion of organic solvent after said thermal treatment step; and wherein the step of adding overhead to organic solvent comprises adding said overhead to at least a portion of recovered organic solvent.

* * * * *